US006432643B1

(12) United States Patent
Einstein et al.

(10) Patent No.: US 6,432,643 B1
(45) Date of Patent: *Aug. 13, 2002

(54) METHOD OF DETERMINING ALZHEIMER'S DISEASE RISK USING APOLIPOPROTEIN E4 GENOTYPE ANALYSIS IN COMBINATION WITH DECREASED ESTROGEN LEVELS

(75) Inventors: Gillian Einstein, Bethesda, MD (US); Laura W. Shaughnessy; Donald E. Schmechel, both of Durham, NC (US)

(73) Assignee: Duke University, Durham, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,650

(22) Filed: Oct. 22, 1999

(51) Int. Cl.⁷ .................... C07H 21/04; C12Q 1/00; C12Q 1/68; C07K 14/00; C07K 14/575
(52) U.S. Cl. ................ 435/6; 435/4; 530/300; 530/350; 530/399; 536/23.1; 536/23.5
(58) Field of Search .............. 435/4, 6, 7.1, 89, 435/91.1, 91.2; 530/350, 399; 536/23.1, 23.5; 600/572

(56) References Cited

U.S. PATENT DOCUMENTS

| | | | |
|---|---|---|---|
| 5,288,717 A | 2/1994 | Raveendranath et al. | ... 514/179 |
| 5,422,119 A | 6/1995 | Casper | ......... 424/449 |
| 5,468,736 A | 11/1995 | Hodgen | ......... 514/179 |
| 5,508,167 A | 4/1996 | Roses et al. | ......... 435/6 |
| 5,565,199 A | 10/1996 | Page et al. | ......... 424/195.1 |
| 5,735,801 A * | 4/1998 | Caillouette | ......... 600/572 |
| 5,773,220 A | 6/1998 | DeKosky et al. | ......... 435/6 |
| 5,916,176 A | 6/1999 | Caillouette | ......... 600/572 |
| 5,935,781 A | 8/1999 | Poirier | ......... 435/6 |

FOREIGN PATENT DOCUMENTS

| WO | WO 95/29257 | 11/1995 |
|---|---|---|
| WO | WO 98/43647 | 10/1998 |
| WO | WO 99/20646 | 4/1999 |

OTHER PUBLICATIONS

Birge, SJ et al. American Journal of Medicine 103(3): 36s–45s, 1997.*
Gauthier, S et al. Alzheimer disease and associated disorders 10(supp 1): 19–21, 1996.*
Henderson, VW. Neurology 48(5 supp 7): s27–s35, 1997.*
Hixson, JE et al. Journal of Lipid Research 31: 545–548, 1990.*
Paganini–Hill, A. et al. American Journal of Epidemiology 140: 256–261, 1994.*
Marx, J. Science 273: 50–53, 1996.*
Poirer, J. et al. Lancet 342: 697–699, 1993.*
Somekawa, Y. et al. European Journal of Obstet Gynecol Reprod Biol 79: 185–191, 1998.*
Srivastava, RA et al. Biochem Mol Biol Int 38(1): 91–101, 1996.*
Tang, M–X, et al. Lancet 348: 429–432, 1996.*
Payami, H. et al. American Journal of Human Genetics 58: 803–811, 1996.*
Shaughnessy et al. The effects of ApoE allelic variation and estrogen deprivation on synapto–dendritic relationships in the hippocampus of aging female transgenic mice. Society Neurosci Ab 25(1–2): 1345, 1999.*
Fox, S. Human Physiology. Dubuque, IA: Wm. C. Brown Publishers, 1990.*
Stone et al.; Increased Synaptic Sprouting in Response to Estrogen via an Apolipoprotein E–Dependent Mechanism: Implications for Alzheimer's Disease, *The Journal of Neuroscience*, 18(9):3180–3185 (1998).
Mirada et al.; Granule Cells in Aging Rats Are Sexually Dimorphic in Their Response to Estradiol, *The Journal of Neuroscience*, 19(9):3316–3325 (1999).
Stone et al.; Abstract: Increased Synaptic Sprouting in Response to Estrogen Via an Apolipoprotein E–dependent Mechanism: Implications for Alzheimer's Disease, *J. of Neuroscience*, 18(9):3180–5 (1998).
Simpkins, et al., The Potential Role of Estrogen Replacement Therapy in the Treatment of the Cognitive Decline and Neurodegeneration Associated with Alzheimer's Disease, *Neurobiology of Aging*, vol. 15, Suppl. 2, pp. 5195–5197 (1994).
Inestrosa, et al., Cellular and Molecular Basis of Estrogen's Neuroprotection, *Molecular Neurobiology*, vol. 17, pp. 73–86 (1998).
Crawford, J.G., Alzheimer's disease risk factors as related to cerebral blood flow: additional evidence, *Medical Hypotheses*, vol. 50, pp. 25–36 (1998).

* cited by examiner

Primary Examiner—Elizabeth C. Kemmerer
Assistant Examiner—Bridget E. Bunner
(74) Attorney, Agent, or Firm—Myers Bigel Sibley & Sajovec

(57) ABSTRACT

A method of screening a subject for risk of developing Alzheimer's disease is carried out by determining the presence of at least one ApoE4 allele in a subject, and determining the presence or absence of decreased estrogen levels in the subject (e.g., due to previous or impending menopause or hysterectomy). The presence of at least one ApoE4 allele (and particularly two ApoE4 alleles) in combination with decreased estrogen levels in the subject indicating the subject is at greater risk of developing Alzheimer's disease (e.g., as compared to subjects with at corresponding number of ApoE4 alleles, but who do not have decreased estrogen levels), and that the subject will receive greater benefit from estrogen replacement therapy in treating Alzheimer's disease than a subject who does not carry one or two ApoE4 alleles.

5 Claims, 2 Drawing Sheets

THERE IS NO DIFFERENCE IN SPINE DENSITY IN THE DORSAL BLADE OF THE DENTATE GYRUS.

CA1 APICAL DENDRITE SPINE DENSITY IS SIGNIFICANTLY DECREASED IN FEMALE APOE4 MICE DEPRIVED OF ESTROGEN.

US 6,432,643 B1

METHOD OF DETERMINING ALZHEIMER'S DISEASE RISK USING APOLIPOPROTEIN E4 GENOTYPE ANALYSIS IN COMBINATION WITH DECREASED ESTROGEN LEVELS

This invention was made with government support under Grant Number 5 T32 AG00029 from the National Institutes of Health. The government has certain rights to this invention.

FIELD OF THE INVENTION

The present invention concerns methods of screening for Alzheimer's disease susceptibility in subjects, along with methods of classifying susceptible individuals for treatment and methods of treating Alzheimer's disease.

BACKGROUND OF THE INVENTION

Alzheimer's disease (AD) is marked by a devastating decrease in cognitive ability which is correlated with a decline in the number of synapses in the hippocampus and neocortex. One of the risk factors for development of AD is the gene coding for the E4 allele of a lipid carrier protein, apolipoprotein E (APOE, gene). The APOE E4 allele is a risk factor for late-onset, familial and sporadic AD while the APOE3 and E2 alleles are either neutral (E3) or protective (E2). Another risk factor is sex; both the incidence and prevalence of AD is greater in females than in males.

U.S. Pat. No. 5,508,167 to A. Roses et al., assigned to Duke University, discloses methods of diagnosing or prognosing Alzheimer's disease in a subject. The methods involve directly or indirectly detecting the presence or absence of an apolipoprotein E type 4 (ApoE4) isoform or DNA, encoding ApoE4 in the subject. The presence of ApoE4 indicates the subject is afflicted with Alzheimer's disease or at risk of developing Alzheimer's disease. This basic finding has led to a number of developments in the Alzheimer's disease field.

For example, U.S. Pat. No. 5,773,220 to S. DeKosy and M. Kamboh, assigned to the University of Pittsburgh, describes a method for screening for the risk of developing Alzheimer's disease in a subject by detecting the presence or absence of the ApoE allele and the presence or absence of the alpha1-antichymotrypsin (ACT) allele. The presence of two ACT/A alleles, in conjunction with the presence of one or two ApoE4 alleles, is said to indicate an increased risk for Alzheimer's disease.

In addition, U.S. Pat. No. 5,935,781 to J. Poirer, assigned to McGill University. This patent describes a method for the identification of human subjects responsive to cholinomimetic therapy. The method comprises determining the absence of apolipoprotein E4 (apoE4) alleles in a biological sample of the patient, where the absence of at least one apoE4 allele indicates a predisposition to respond to cholinomimetic therapy. Methods of administering cholinomimetics to such identified subjects are also described.

While the identification of ApoE4 as a risk factor for Alzheimer's disease has led to a number of new developments in the field, AD remains a complex disease for which treatment is difficult and the ultimate prognosis is poor. Accordingly, there remains a need for new ways to screen for AD, classify patients for appropriate AD treatment, and treat AD.

SUMMARY OF THE INVENTION

A first aspect of the present invention is a method of screening (e.g., diagnosing or prognosing) a subject for risk of developing Alzheimer's disease. The method comprises: (a) determining the presence of at least one ApoE4 allele in a subject, and (b) determining the presence or absence of decreased estrogen levels in said subject. The presence of at least one ApoE4 allele (and particularly two ApoE4 alleles) in combination with decreased estrogen levels in said subject indicating said subject is at greater risk of developing Alzheimer's disease (e.g., as compared to subjects with at corresponding number of ApoE4 alleles, but who do not have decreased estrogen levels).

A second aspect of the present invention is a method for screening a subject for responsiveness to estrogen replacement therapy for the treatment of Alzheimer's disease. The method comprises determining the presence of at least on ApoE4 allele in the subject. The presence of at least one apoE4 gene allele allele (and particularly two ApoE4 alleles) indicates that the subject will receive greater benefit from estrogen replacement therapy that a subject who does not carry at least one ApoE4 allele allele (and particularly two ApoE4 alleles). Alternatively stated, the presence of at least one ApoE4 allele indicates a predisposition, or potential, of that subject to beneficially respond to estrogen replacement therapy (e.g., a greater likelihood that that subject will beneficially respond to estrogen replacement therapy as compared to a subject that does not carry at least one ApoE4 allele).

A third aspect of the present invention is a method for treating a subject for Alzheimer's disease. The method comprises: (a) determining the presence of at least one ApoE4 allele in said subject allele (and particularly two ApoE4 alleles); and then (b) administering estrogen replacement therapy to that subject (i.e., a subject carrying one or two ApoE4 alleles) in an Alzheimer's disease treatment effective amount.

A fourth aspect of the present invention is a method of treating a human female subject for Alzheimer's disease, where that subject carries at least one ApoE4 allele allele (and particularly two ApoE4 alleles). The method comprises administering estrogen replacement therapy to the subject in an Alzheimer's disease treatment effective amount.

In a particularly preferred embodiment, the estrogen replacement therapy is initiated to a susceptible subject as described above prior to the onset of menopause, or at least concurrently with the onset of menopause, or is initiated concurrently with a hysterectomy. The object in this embodiment is to reduce, inhibit, or eliminate a gap in estrogen levels, or the time for which the subject is exposed to decreased estrogen levels, so that the risk of early neuronal cell death in that patient is reduced, and the time of onset of Alzheimer's disease is delayed, and/or the progression of that disease is slowed.

A fifth aspect of the present invention is the use of an estrogen replacement therapy active agent for the preparation of a medicament for the treatment of Alzheimer's disease.

The foregoing and other objects and aspects of the present invention are explained in detail in the drawings herein and the specification set forth below.

DETAILED DESCRIPTION OF THE PREFERRED EMBODIMENTS

Figure 1:
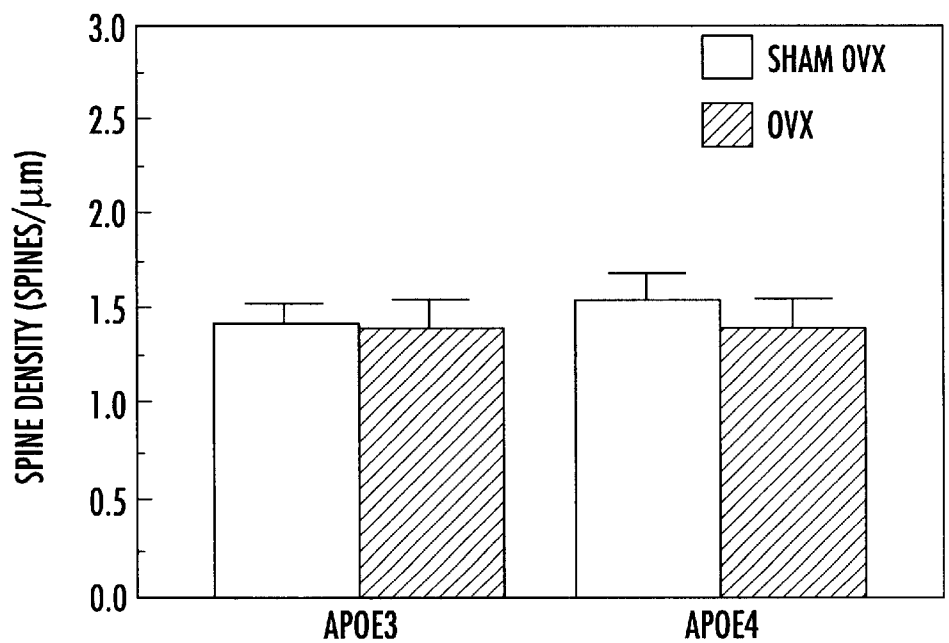
FIG. 1 shows that there is no difference in spine density in the dorsal blade of the dentate gyrus in ApoE3 as compared to ApoE4 mice, comparing Sham OVX and OVX mice.

Terms and phrases used herein have their ordinary meaning in the art, as further explained below.

"ApoE4" refers to apolipoprotein E4.

"Concurrently" as used herein means at the same time or sufficiently close in time that substantially the same physiological effect is achieved.

"Estrogen replacement therapy" as used herein refers to a long-term therapy in which estrogen or estrogenic active agents are administered to a subject continuously over an extended period of time (e.g., a month, a year, or more) to maintain sustained blood levels of the active agent to combat the effects of menopause or hysterectomy (e.g., loss of calcium from bone and increased incidence of classical osteoporotic fractures of the forearm and hip, ischemic heart disease, etc.). The administration may be daily or periodically.

"Decreased estrogen levels" as used herein means that the subject has estrogen levels indicating that the subject is a candidate for or should receive estrogen replacement therapy (e.g., an estrogen level at a post-menopausal rather than a pre-menopausal level; an estrogen level at a post-hysterectomy rather than a pre-hysterectomy level in a pre-menopausal woman)

Subjects suitable for the present invention include those who have not previously been diagnosed as afflicted with Alzheimer's disease, those which have previously been determined to be at risk of developing Alzheimer's disease, and those who have been initially diagnosed as being afflicted with Alzheimer's disease where confirming information is desired, or where a focused treatment option is desired. For example, patients diagnosed or determined to be afflicted with dementia, particularly patients who had previously been clinically normal who are determined to be afflicted with a progressive dementia, are suitable subjects. Thus, the present invention may be employed in detecting both familial Alzheimer's disease (late onset and early onset) as well as sporadic Alzheimer's disease. Many Alzheimer's disease patients encountered in practice have no obvious family history and have been classified as sporadic. However, genetic factors in early- and late-onset of familial Alzheimer's disease (FAD) are well documented. Late-onset Alzheimer's disease is the classification usually used if the disease is diagnosed to occur after the age of 65 in humans. The present invention is particularly useful in identifying patients who would benefit from the early administration of an estrogen replacement therapy. Subjects suitable for the present invention are, in general, human subjects, and are preferably female subjects.

The step of detecting the presence or absence of ApoE4 or of DNA encoding such isoform (including the number of alleles for ApoE4) may be carried out either directly or indirectly by any suitable means. A variety of techniques are known to those skilled in the art. All generally involve the step of collecting a sample of biological material containing either DNA or ApoE from the subject, and then detecting whether or not the subject possesses ApoE4 or DNA encoding such isoform from that sample. For example, the detecting step may be carried out by collecting an ApoE sample from the subject (for example, from cerebrospinal fluid, or any other fluid or tissue containing ApoE), and then determining the presence or absence of an ApoE4 isoform in the ApoE sample (e.g., by-isoelectric focusing or immunoassay). In the alternative, the detecting step may be carried out by collecting a biological sample containing DNA from the subject, and then determining the presence or absence of DNA encoding an ApoE4 isoform in the biological sample. Any biological sample which contains the DNA of that subject may be employed, including tissue samples and blood samples, with blood cells being a particularly convenient source. Numerous techniques for detecting the presence of one or two ApoE4 alleles in a subject are known, including but not limited to those described in U.S. Pat. No. 5,508,167 to Roses et al., U.S. Pat. No. 5,773,220 to S. DeKosy and M. Kamboh, and U.S. Pat. No. 5,935,781 to Poirer (applicants specifically intend that the disclosures of all United States patent references cited herein be incorporated herein by reference).

Patients may be selected for treatment by the methods of the present invention based upon knowledge of the ApoE4 profile of that individual patient (i.e., the presence of one or two ApoE4 alleles). The ApoE profile may be obtained in the manner described above. Of course, it is not necessary that such screening or profiling be at the same time or place, or by the same individual, as making the selection for therapy, so long as the selection is based upon this information.

Estrogen replacement therapy may be carried out by any suitable means. All typically involve administering an active agent such as estrogen or an estrogen analog (typically a steroid that has estrogen activity) to the subject in an estrogen replacement therapy effective amount, which is commensurate with an Alzheimer's disease treatment effective amount (e.g., an amount effective to delay the onset of AD, slow the progression of AD, etc.). Any suitable route of administration may be employed, including, but not limited to, oral administration, aerosol administration to airway surfaces, intravenous injection, subcutaneous injection, intramuscular injection, transdermal administration (e.g., a patch), etc. Oral and transdermal formulations are currently preferred. Numerous estrogen replacement therapy preparations and protocols are known, including but not limited to those described in U.S. Pat. Nos. 5,922,349; 5,897,539; 5,565,199; 5,468,736; 5,422,119; 5,288,717; and 5,023,084, the disclosures of all of which are incorporated by reference herein in their entirety. Other agents, such as progesterone (or progestin) in a hormone replacement therapy effective amount, may be administered along with the estrogen to provide a combination therapy, if desired (typically to reduce undesirable side-effects of estrogen monotherapy, as such estrogenic endometrial proliferation and corresponding risk of endometrial cancer).

Suitable active agents for estrogen replacement therapy include, but are not limited to, natural and synthetic estrogens such as conjugated equine estrogen, ethinyl estradiol, micronized estradiol, 17β estradiol, mestranol, estradiol valerate, 11-nitrato estradiol, 7-α-methyl-11-nitrato-estradiol, piperazine estrone sulfate, quinestranol, and 8,9-dehydroestereone (particularly alkali metal salts and sulfate esters thereof). See, e.g., U.S. Pat. No. 5,422,119 at column 6; U.S. Pat. No. 5,288,717. Of course, all active agents may be prepared as a pharmaceutically acceptable salt or ester, in accordance with known techniques, The progestin component may be any progestationally active compound, including but not limited to progsterone, 17-hydroxyprogesterone, dihydroprogesterone, medroxyprogesterone acetate, norethindrone, norethindrone acetate, norethynodrel, ethynodioldiacetate, norgesterel, levo-norgesterel, gestodene, delta-15-levonorgesterel, norgestimate, 17-deacetyl norgestimate, nomegestereol, nesterone, desogesterel and 3-keto-desogesteral. See, e.g., U.S. Pat. No. 5,422,119 at column 6.

In general, a pharmaceutical formulation or medicament for estrogen replacement therapy is prepared by bringing an effective of the active agent into contact with a pharmaceutically acceptable carrier, such as lactose or talc (for an oral administration), intimately admixing the two, and forming (when necessary) the mixture into a suitable unit dosage form such as a patch for transdermal administration or a tablet, dragee, capsule or pill for an oral dosage form.

The amount of active agent administered will depend upon factors such as the specific active agent, the age, weight and condition of the subject, the route of administration, etc. For example, the estrogenic active agent may be administered in an a amount of from 0.3 to 1.2 mg daily for orally administered conjugated equine estrogen; or from about 25 µg/day to about 150 µg/day of transdermal β-estradiol.

Examples of commercially available estrogen preparations include: Alora™ (skin patch), Climara™ (skin patch), Estraderm™ (skin patch), FemPatch™ (skin patch), Estrace™ (pill or skin patch), Estrab™ (pill), Menset™ (pill), Ogen™ (pill), Ortho-est™ (pill), and Premarin™ (pill)

Examples of commercially available estrogen/progestin combination formulations include, but are not limited to, Combipatch™ (skin patch) and Prempro™ (pill).

Where necessary, estrogen levels may be directly or indirectly determined in a subject by measuring serum estradiol levels in accordance with known techniques, or by measuring vaginal or urethral pH levels, as described in U.S. Pat. No. 5,916,176 to Caillouette. Of course, decreased estrogen levels may be inferred from menopause or hysterectomy.

The present invention is illustrated in greater detail in the following non-limiting examples.

EXAMPLE 1
Effect of Ovarectomy on Spine and Hippocampal Neuron Density in Transgenic ApoE4 and ApoE3 Mice This example explored whether the interaction of the ApoE4 risk factor and the estrogen risk factor might exacerbate the pathology associated with AD in a putative animal model of AD. To explore this possibility, we compared spine and synapse density in two populations of hippocampal neurons in 15-month-old human transgenic APOE4 and APOE3 mice ovariectomized (OVX) or sham OVX mice at 14 months of age. CA1 pyramidal neurons are one of the most susceptible populations of neurons in AD, while dentate granule cells are less vulnerable.

Animals and Surgery. Female transgenic mice created from the C57B1/6J line with the human isoforms of APOE3 and APOE4 were used (P.-T. Xu et al., *Neurobiol. Dis.* 3, 229–235 (1996). Three sibling pairs were obtained for each group. At 14 months of age, one member of each pair was ovariectomized (OVX) while the other member received a sham OVX surgery.

Tissue Preparation. At 15 months of age, all animals were euthanized, their brains removed and cut along the midline. Each brain was immersion-fixed in 4% paraformaldehyde in 0.1 M phosphate buffer (PB), pH 7.4, at room temperature (RT). After 140 minutes, the left hemisphere was removed and rinsed in 0.1 M PB. Using a vibratome, sagittal slices of 300 microns were collected in 0.1 M PB and stored at 40° C. until intracellular injection with Lucifer yellow. The right hemisphere was immersion-fixed for 48 hours at 4° C., embedded in paraffin, and sectioned sagittally into 8 micron slices that were mounted on slides in preparation for synaptophysin immunohistochemistry (SYN-IR).

Lucifer Yellow injections and immunoreactivity. Hippocampal CA1 pyramidal cells and dentate granule cells were injected intracellularly with Lucifer yellow in accordance with known techniques (G. Einstein, *J. Neurosci. Meth.* 26, 95–103 (1988)). At least three slices from the dorsal hippocampus were injected per animal, with 10–15 granule cells and CA1 neurons injected per slice.

After injection, slices were rinsed in PB and post-fixed overnight in 10% formalin. The tissue was then put in 25% sucrose (in 0.1M phosphate buffered saline-PBS) for cryoprotection and resectioned at 60 microns on a freezing microtome. Free-floating sections were rinsed in PBS, blocked, incubated in biotinylated anti-Lucifer-yellow antibody followed by incubation in ABC and visualization with DAB. The tissue was mounted on gelatin-subbed slides and coverslipped. Under a 100X objective and using a drawing tube, four neurons each from CA1 and the dorsal blade of the dentate gyrus were drawn and the spines counted.

Synaptophysin immunoreactivity. Slides containing sections through the dorsal hippocampus were incubated with the mouse monoclonal antibody to synaptophysin followed by incubation with a biotinylated secondary antibody, an ABC solution and then visualized using DAB (E. Masliah et al., *Exp. Neurol.* 113, 131 (1991)). Following coverslipping, images of the stratum radiatum and molecular layers of the dentate were grabbed using an MTI camera and the imaging program Image 1. NIH Image 1.63 was used to analyze the density of synaptophysin staining in each of these areas.

Table 1 below shows that there is no difference in the optical density of SYN-IR for the molecular layers of the dorsal blade of the dentate gyrus.

TABLE 1

| GROUP | inner molecular layer | middle molecular layer | outer molecular layer |
|---|---|---|---|
| APOE3 SHAM | 44.92 ± 7.8 | 37.50 ± 6.8 | 42.95 ± 5.1 |
| APOE3 OVX | 49.60 ± 5.6 | 42.50 ± 5.0 | 45.90 ± 4.5 |
| APOE4 SHAM | 46.10 ± 5.7 | 33.40 ± 5.0 | 42.50 ± 7.1 |
| APOE4 OVX | 48.96 ± 4.1 | 37.20 ± 3.0 | 44.37 ± 4.3 |

Figure 2:
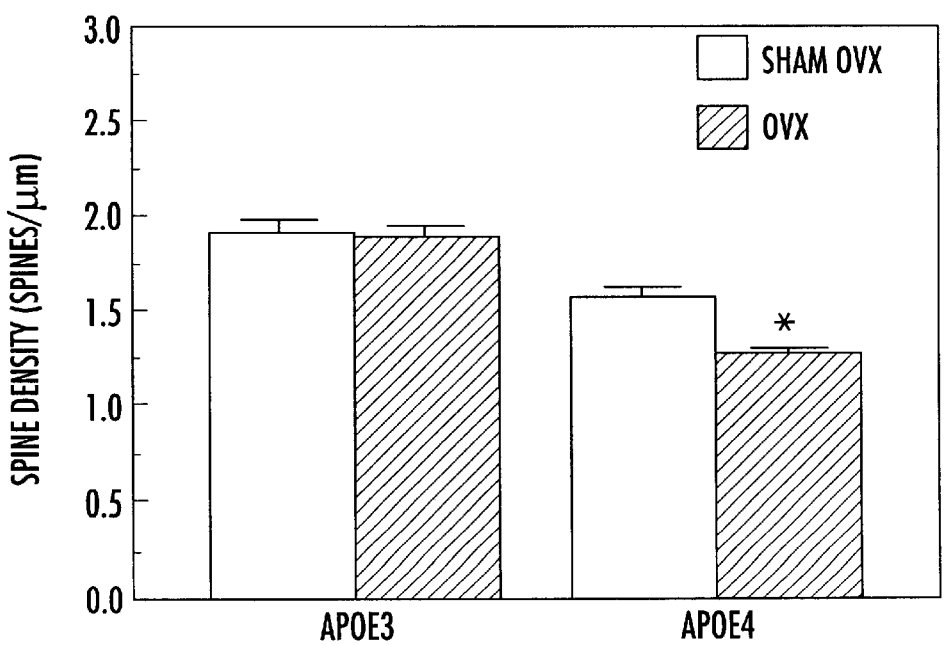
FIG. 2 illustrates that CA1 apical dendrite spine density is significantly decreased in female ApoE4 mice deprived of estrogen.
Figure 3:
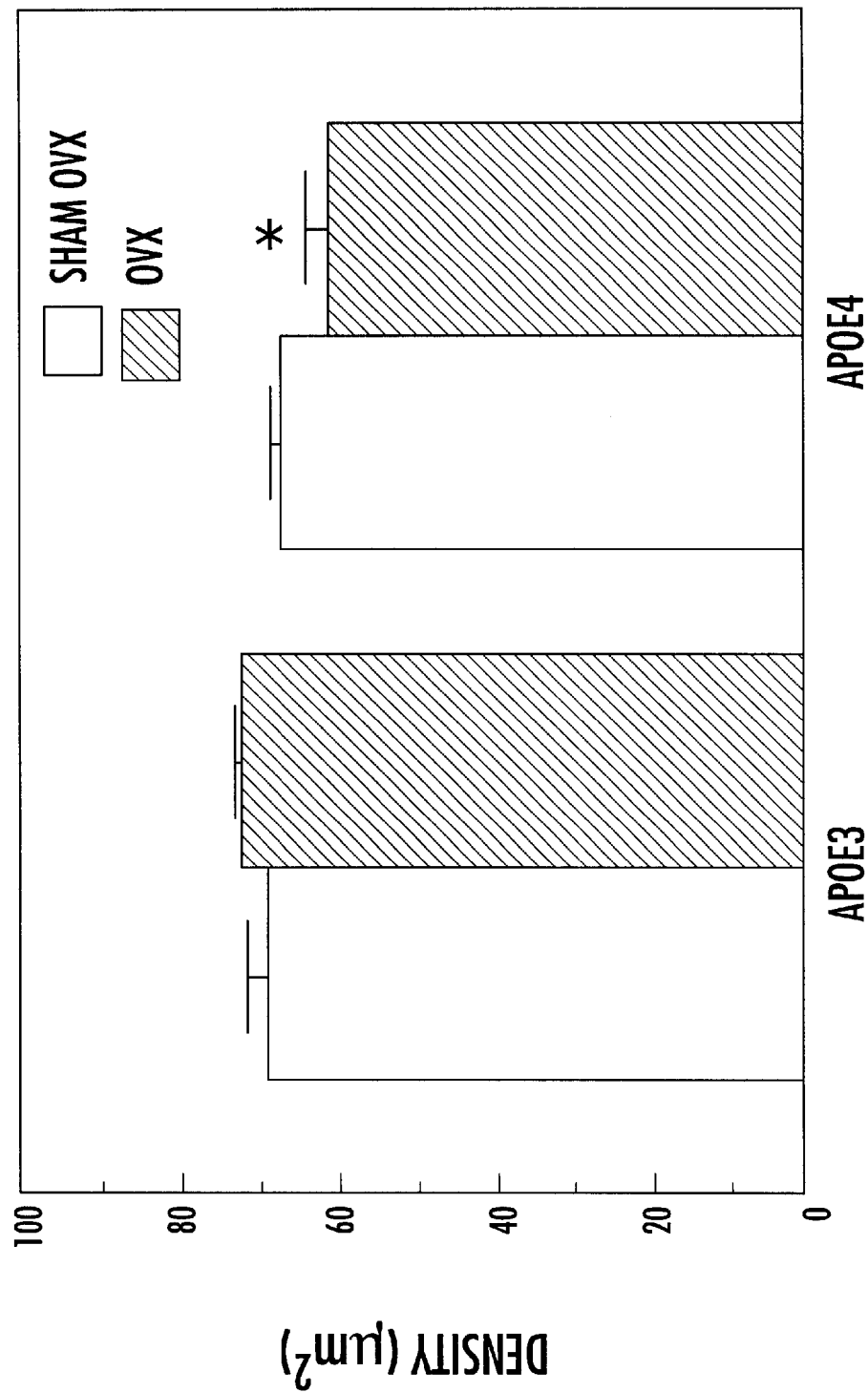
FIG. 3 shows that stratum radiatum synapthophysin immunoreactivity is significantly decreased in ApoE4 mice deprived of estrogen.

FIG. 1 shows that there is no difference in spine density in the dorsal blade of the dentate gyrus in ApoE3 as compared to ApoE4 mice, comparing Sham OVX and OVX mice. FIG. 2 illustrates that CA1 apical dendrite spine density is significantly decreased in female ApoE4 mice deprived of estrogen. FIG. 3 shows that stratum radiatum synaptophysin immunoreactivity is significantly decreased in ApoE4 mice deprived of estrogen.

Observations. (1) With our paradigm, mice carrying the APOE4 gene had a significant decrease in spine density on the apical dendrites of CA1 pyramidal neurons when compared to sham OVX sibs. In contrast, mice carrying the APOE3 gene had no change in spine density of CA1 pyramidal neurons when compared to sham OVX sibs. (2) Mice carrying the APOE4 gene had a significant decrease in the density of SYN-IR in the stratum radiatum when compared to sham OVX sibs. In contrast, mice carrying the APOE3 gene had no change in the density of SYN-IR in the stratum radiatum when compared to sham OVX sibs. (3) Mice carrying the APOE3 and E4 gene had no change in spine density of dorsal blade dentate granule cells when compared to sham OVX sibs. (4) Mice carrying the APOE3 and E4 gene had no change in the density of SYN-IR in the molecular layer of the dentate when compared to sham OVX sibs.

These data show that the most vulnerable population of neurons is the CA1 neurons in the aging APOE4 mice deprived of estrogens. The decrease in both spine and SYN-IR density indicate a significant decrease in synapses and in neuronal connectivity. The interaction of the two risk factors, APOE4 and estrogen deprivation, exacerbates the pathology associated with AD.

The foregoing is illustrative of the invention, and is not to be construed as limiting thereof. The invention is defined by the following claims, with equivalents of the claims to be included therein.

We claim:

1. A method of determining when estrogen replacement therapy should be initiated in a premenopausal human female subject at risk of developing Alzheimer's disease, comprising:
   (a) determining the presence of at least one ApoE4 allele in a premenopausal human female subject, and
   (b) determining prior to the onset of menopause the presence or absence of a future decreased estrogen level in said subject due to (i) onset of menopause or (ii) a hysterectomy in said subject; and then
   (c) initiating estrogen replacement therapy in said subject prior to said onset of menopause or concurrently with said hysterectomy if at least one ApoE4 allele is determined to be present in said subject.

2. A method according to claim 1, wherein said step of determining the presence of at least one ApoE4 allele is carried out by collecting a biological sample containing DNA from said subject, and then detecting the presence or absence of DNA encoding ApoE4 in said biological sample.

3. A method according to claim 2, wherein said detecting step is carried out by amplifying DNA encoding ApoE4.

4. A method according to claim 1, wherein said determining step comprises detecting whether said subject is homozygous for the gene encoding ApoE4.

5. The method according to claim 1, wherein said estrogen replacement therapy further comprises the step of administering progestin to said subject.

* * * * *